United States Patent [19]
Malchesky

[11] Patent Number: 5,928,948
[45] Date of Patent: Jul. 27, 1999

[54] METHOD FOR THE ASSESSMENT AND VALIDATION OF CLEANING PROCESSES

[75] Inventor: Paul S. Malchesky, Painesville Township, Ohio

[73] Assignee: Steris Corporation, Mentor, Ohio

[21] Appl. No.: 08/814,804

[22] Filed: Mar. 10, 1997

[51] Int. Cl.$^6$ .................................................. C12M 1/00
[52] U.S. Cl. .................. 436/2; 422/28; 422/40; 422/82.05; 422/82.09; 436/5; 436/27; 436/28; 436/31; 436/56; 73/60.11; 250/339.11; 250/339.12; 250/341.8
[58] Field of Search .......................... 422/28, 40, 82.05, 422/82.09; 436/2, 5, 27, 28, 31, 56; 73/60.11; 250/339.11, 339.12, 341.8; 8/158

[56] References Cited

U.S. PATENT DOCUMENTS

| D. 345,829 | 4/1994 | Mancuso et al. | 40/1 |
|---|---|---|---|
| 3,243,377 | 3/1966 | Stolar et al. | 252/95 |
| 3,608,514 | 9/1971 | Dunn | 116/118 |
| 3,697,573 | 10/1972 | Danzik et al. | 260/457 |
| 3,861,413 | 1/1975 | Woehler | 137/334 |
| 3,925,010 | 12/1975 | Barton | 8/142 |
| 4,016,089 | 4/1977 | Regan et al. | 252/106 |
| 4,018,696 | 4/1977 | Hellsten et al. | 252/89 R |
| 4,078,943 | 3/1978 | Saurenman | 134/14 |

(List continued on next page.)

FOREIGN PATENT DOCUMENTS

| 9647177 | 8/1996 | Australia . |
|---|---|---|
| 553 519 A1 | of 0000 | European Pat. Off. . |
| 278360 | 8/1988 | European Pat. Off. . |
| 705573 | 4/1996 | European Pat. Off. . |
| 3418920 | 1/1986 | Germany . |
| 3713899 | 4/1987 | Germany . |
| 4219244 | 12/1993 | Germany . |
| 4435223 | 4/1996 | Germany . |
| 19502133 | 8/1996 | Germany . |

(List continued on next page.)

OTHER PUBLICATIONS

Hawley's Condensed Chemical Dictionary, 11th Edition, 1987, p. 940.

Robert T. Tucker, et al., vol. 42, No. 4, Surface Analysis of Clincially Used Expanded PTFE Endoscopic Tubing Treated By the Steris Process, ASAIO Journal 1996, pp. 306–313, (Jul.–Aug., 1996).

Herr Aebi, et al., Testing and Evaluating the Cleaning and Disinfection Efficacy of Endoscope Washer/Disinfectors and Disinfection Automats, pp. 40–47, Hyg. Med. vol. 20. (1995).

Dr. Paul Malchesky, Reprocessing of Reusable Medical Devices, ASAIO Journal, pp. 146–151, (Apr.–Jun. 1995).

Andersen HK, et al., Decontamination of dental equipment. A validation of three devices designed for cleaning, disinfecting, and lubricating of dental high–speed turbines and handpieces, Zentralbl Hyg Umweltmed, pp. 437–443, (Jan. 1995).

Roth K. et al., Automated processing of endoscopic surgical instruments, Dept. of General Surgery, Eberhard–Karls Unviersitiy Tuebingen, Germany, pp. 279–281, (Oct. 1994).

*Primary Examiner*—Harold Y. Pyon
*Assistant Examiner*—S. Carrillo
*Attorney, Agent, or Firm*—Fay, Sharpe, Beall, Fagan, Minnich & McKee

[57] ABSTRACT

A porous material (10) is contaminated with soil (14). Optionally, the porous material is partially shielded by an impermeable layer. The contaminated porous material is packaged and shipped to a user site. The contaminated porous material is removed from the package and placed in an automated processor containing medical equipment (22). The medical equipment and porous material are subjected to a cleaning, disinfecting, or sterilizing cycle in the processor. The cleaning process is evaluated by examining the porous material with an infrared or other electronic reader (24) to determine the presence of remaining soil which has not be removed during the cleaning, disinfecting, or sterilizing cycle.

14 Claims, 3 Drawing Sheets

U.S. PATENT DOCUMENTS

| | | | |
|---|---|---|---|
| 4,087,326 | 5/1978 | Kereluk | 195/103.5 R |
| 4,137,044 | 1/1979 | Flower | 8/137 |
| 4,336,223 | 6/1982 | Hillman | 422/24 |
| 4,407,960 | 10/1983 | Tratnyek | 436/2 |
| 4,431,560 | 2/1984 | Lake et al. | 252/142 |
| 4,461,837 | 7/1984 | Karle et al. | 435/296 |
| 4,482,634 | 11/1984 | Davis, Jr. et al. | 436/31 |
| 4,489,574 | 12/1984 | Spendel | 68/16 |
| 4,576,650 | 3/1986 | Yabe et al. | 134/22.12 |
| 4,579,715 | 4/1986 | Bruso | 422/58 |
| 4,636,472 | 1/1987 | Bruso | 435/287 |
| 4,668,475 | 5/1987 | Meloy | 422/37 |
| 4,692,307 | 9/1987 | Bruso | 422/58 |
| 4,710,233 | 12/1987 | Hohmann et al. | 134/1 |
| 4,743,537 | 5/1988 | McCormick et al. | 435/296 |
| 4,836,949 | 6/1989 | Klajnscek | 252/135 |
| 4,839,291 | 6/1989 | Welsh et al. | 435/269 |
| 4,863,627 | 9/1989 | Davies et al. | 252/95 |
| 4,872,235 | 10/1989 | Nielsen | 15/104.92 |
| 4,903,718 | 2/1990 | Sullivan | 134/184 |
| 4,918,003 | 4/1990 | Macaro et al. | 435/31 |
| 4,988,485 | 1/1991 | Bene | 422/292 |
| 5,055,215 | 10/1991 | Mairs et al. | 252/90 |
| 5,067,983 | 11/1991 | Uchino | 134/1 |
| 5,093,079 | 3/1992 | Bakaitis et al. | 422/28 |
| 5,110,367 | 5/1992 | Ahlstrom | 134/42 |
| 5,112,520 | 5/1992 | Krinski et al. | 252/174.23 |
| 5,133,374 | 7/1992 | Druding et al. | 134/104.2 |
| 5,204,062 | 4/1993 | Buglino et al. | 422/56 |
| 5,234,832 | 8/1993 | Disch et al. | 435/264 |
| 5,238,660 | 8/1993 | Dietwart | 422/295 |
| 5,238,843 | 8/1993 | Carpenter et al. | 435/264 |
| 5,251,356 | 10/1993 | Oaki et al. | 15/104.095 |
| 5,274,874 | 1/1994 | Cercone et al. | 15/244.1 |
| 5,288,467 | 2/1994 | Biermaier | 422/116 |
| 5,308,579 | 5/1994 | Melon et al. | 422/28 |
| 5,311,891 | 5/1994 | Uchino | 134/46 |
| 5,338,748 | 8/1994 | Wachman et al. | 514/358 |
| 5,346,889 | 9/1994 | Tsuchiya et al. | 514/21 |
| 5,366,872 | 11/1994 | Hird et al. | 435/31 |
| 5,382,297 | 1/1995 | Valentine et al. | 134/15 |
| 5,403,505 | 4/1995 | Hachmann et al. | 252/106 |
| 5,405,580 | 4/1995 | Palmer | 422/28 |
| 5,421,813 | 6/1995 | Ohnishi | 604/4 |
| 5,425,815 | 6/1995 | Parker et al. | 134/26 |
| 5,494,531 | 2/1996 | Azuma | 134/25.4 |
| 5,516,648 | 5/1996 | Malchesky et al. | 435/31 |
| 5,518,927 | 5/1996 | Malchesky et al. | 436/1 |
| 5,529,788 | 6/1996 | De Senna | 424/466 |
| 5,533,539 | 7/1996 | Sutter et al. | 134/95.2 |
| 5,547,635 | 8/1996 | Duthie, Jr. | 422/24 |
| 5,551,462 | 9/1996 | Biermaier | 134/166 C |
| 5,552,115 | 9/1996 | Malchesky | 422/28 |
| 5,552,320 | 9/1996 | Smith | 422/28 |
| 5,554,228 | 9/1996 | Giordano et al. | 134/21 |
| 5,571,488 | 11/1996 | Beerstecher et al. | 422/297 |
| 5,620,656 | 4/1997 | Wensky et al. | 422/28 |
| 5,651,276 | 7/1997 | Purer et al. | 68/5 C |
| 5,676,705 | 10/1997 | Jureller et al. | 8/142 |

FOREIGN PATENT DOCUMENTS

| | | |
|---|---|---|
| 29612976 | 9/1996 | Germany . |
| 19153994 | 10/1996 | Germany . |
| 62180100 | 8/1987 | Japan . |
| 62193686 | 8/1987 | Japan . |
| 2080049 | 3/1990 | Japan . |
| 90055113 | 11/1990 | Japan . |
| 6285437 | 10/1994 | Japan . |
| 6312011 | 11/1994 | Japan . |
| 8157888 | 6/1996 | Japan . |
| 9209570 | 10/1992 | Rep. of Korea . |
| 2041719 | 8/1995 | Russian Federation . |
| 2289512 | 11/1995 | United Kingdom . |
| 2292888 | 3/1996 | United Kingdom . |
| 9313861 | 9/1993 | WIPO . |
| 9624385 | 8/1996 | WIPO . |

5,928,948

METHOD FOR THE ASSESSMENT AND VALIDATION OF CLEANING PROCESSES

BACKGROUND OF THE INVENTION

The present invention relates to the washing; decontamination and sterilization arts. It finds particular application in conjunction with cleaning apparatus for medical, dental, surgical veterinary, and other devices and equipment and will be discussed with particular reference thereto. It is to be appreciated, however, that the invention is also applicable to washing, decontaminating or sterilizing devices and equipment in other fields.

Reusability of medical devices is becoming increasingly important in an effort to provide cost effective health care. Traditionally, the effectiveness of processes for cleaning medical equipment has been assessed by measuring the ability of the process to sterilize the processed items. Frequently, a biological or chemical indicator is included with the process load. After completion of the process cycle, the indicator is evaluated to give a measure of the effectiveness of the cycle in terms of an estimation of the likelihood that microorganisms present in the load have been destroyed.

Recently, it has been shown that for many purposes, killing efficiency is not a complete measure of the decontamination process. Non-living, organic contamination may remain on the apparatus which is not detected by chemical and biological indicators. This contamination, known as soil, includes biological materials such as dried blood, mucous, feces, saliva, and bile. This soil can compromise the efficient use of the device or inhibit its sterilization and lead to infections when the equipment is reused. In particular, microorganisms that have been destroyed in the decontamination process, but which remain on the surfaces of the apparatus, can be a health hazard. The dead remains of those microorganisms degrade to form products which are harmful to humans. For example, the walls of Gram negative bacteria degrade to form endotoxins which can cause pyrogenic reactions in patients with which the equipment is used.

In addition, materials such as blood and other medical wastes, which remain on medical equipment, provide sites which encourage microorganisms to grow. Further, if the soil is not thoroughly removed during the cleaning process, it may become fixed to the surface of the apparatus in such a manner that makes future cleaning difficult if not impossible. For example, glutaraldehyde solutions, used for the disinfection of medical devices, have been shown to create a layer of cross-linked soil on endoscopes which proves to be highly resistant to removal. Robert C. Tucker, Brian J. Lestini & Roger E. Marchant, ASAIO J. Vol. 42, No. 4 (1996) p. 306. Residual soil also hinders the ability of subsequent sterilization or disinfection processes to destroy infectious microorganisms by insulating the organisms from the sterilant or disinfectant and impeding penetration.

In one technique to assess the ability of a cleaning process to remove soils, two metal plates are soiled, clipped together, and subjected to the cleaning cycle. Removal of the soil is an indication that the cleaning process has been effective. A protrusion on one end of one of the plates creates a variably sized crevice between the plates when the two are sandwiched together. This could allow an estimate of the degree of cleaning if the soil is removed from only a portion of the crevice, usually the wider part.

Although the metal plate method gives an indication of the effectiveness of cleaning, it may not simulate the more challenging examples of medical equipment requiring cleaning, such as endoscopes. Medical equipment currently in use often contains designs, which readily absorb medical soils and do not release them easily during the cleaning process. Moreover, although a rough assessment of the effectiveness of cleaning may be made visually, the method is not readily amenable to accurate assessment of the extent of soil remaining.

The present invention provides a new and improved apparatus and method for testing the effectiveness of soil removal which overcomes the above referenced problems and others. The method may be used both for process validation testing and for periodic testing of the cleaning apparatus in use.

SUMMARY OF THE INVENTION

In accordance with one aspect of the invention, an apparatus for the assessment and validation of a cleaning process is provided. A porous material, resistant to destruction by the cleaning process is contaminated with a known soil.

In accordance with another aspect of the present invention, a method for the assessment and evaluation of a cleaning process is provided. A porous material is contaminated with a known soil. The contaminated porous material is subjected to a cleaning process. The porous material is then evaluated for remaining soil.

One advantage of the present system is that it enables the effectiveness of a cleaning process to be evaluated.

Another advantage of the invention is that it can assure cleanliness.

Another advantage of the present system is that it enables optimum cleaning conditions and the selection of optimum cleaning agents and processes to be determined.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
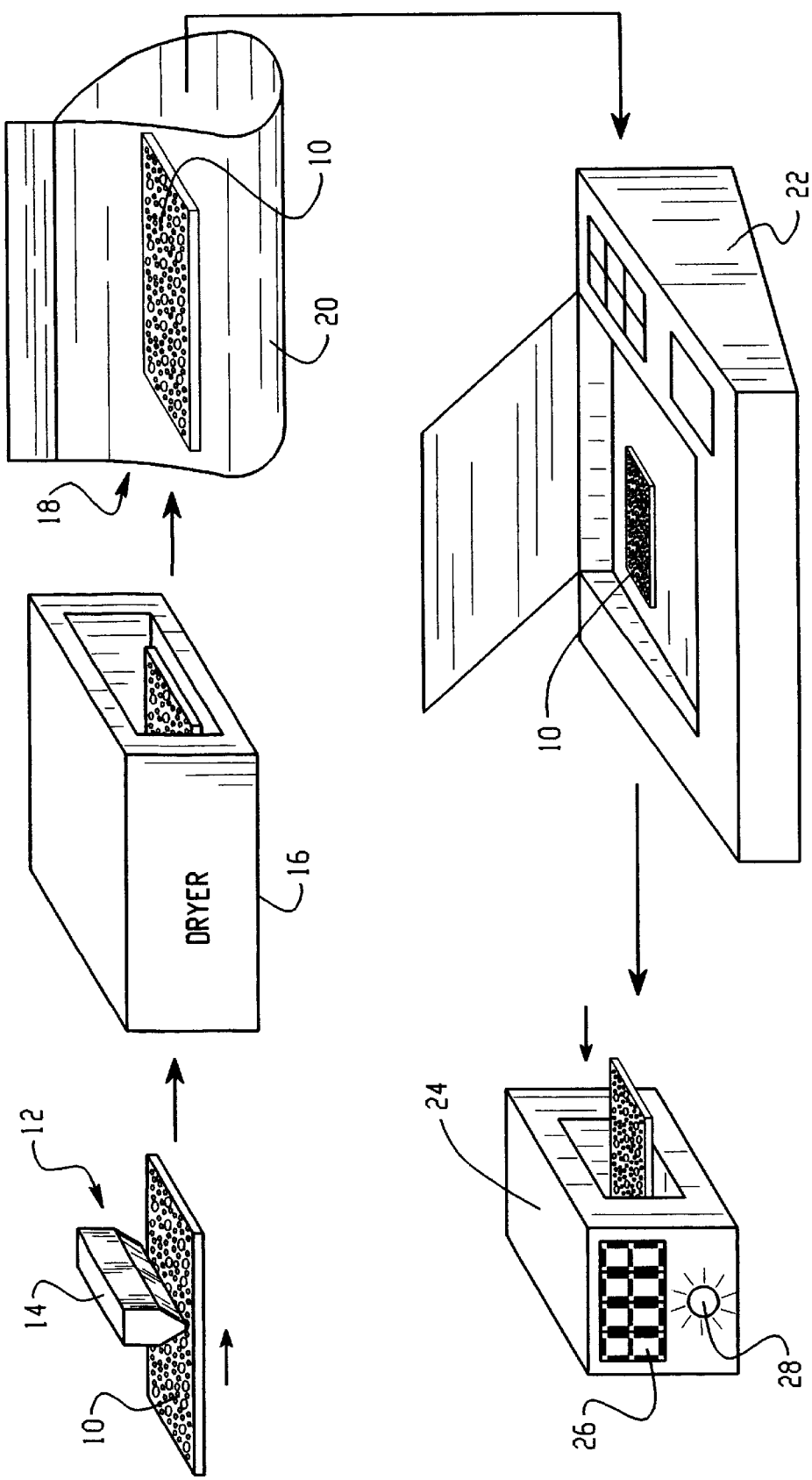
FIG. 1 illustrates a method of monitoring cleanliness in accordance with the present invention.

With reference to FIG. 1, porous material 10 is contaminated 12 with soil. Preferably, the soil is applied in a slurry for easier handling. Optionally, the soil is dried 16 to emulate dried soil in other applications in which it is desirable to check for the removal of damp or water containing soils, the drying step is omitted. Preferably the porous material 10 is packaged 18 in a sealed package 20 which prevents contamination of the material with foreign soil and which maintains the controlled moisture level within the porous material. The soiled porous material is placed in a processor 22 at the beginning of a cleaning, disinfecting, or sterilizing cycle. The soiled material may be placed in the processor by itself to validate the processor. Alternately, the soiled material may be placed in the processor along with a load of analogously soiled instruments. After the process is complete, the soiled material is removed from the processor 22 and examined for cleanliness. Preferably, the material is placed in an electronic reader 24 which examines the soiled material and assesses its cleanliness. The assessment is displayed on a gauge 26 or with a warning light 28. The warning light might be a green light to indicate a satisfactory level of cleaning or a red light for indicating an unsatisfactory level of cleaning.

Preferably the soil 14 is selected to represent the type of contamination that the cleaning process or 22 is required to remove. The soil may be one of a number of composite standard, or "synthetic," soils that are commercially available, or could be formulated from known recipes such as HUCKER'S SOIL, EDINBURG SOIL or V.A. SOIL. Alternatively, samples of protein or other biological materials may be used, including blood, mucous, feces, saliva and bile. Preferably the soil is added to the porous material as a slurry and then dried, although other methods of application are contemplated. Drying renders the soil move difficult to be removed, and thus representative of contaminated medical equipment which may have been left for some time before cleaning.

In one preferred embodiment, the soil is added to the porous material during manufacturing, before the packaging 18 of the apparatus. The reproducibility in the quantity of soil added and method of drying applied is thereby improved. In another preferred embodiment, the soil is added to the porous material by the user of the cleaning process. This allows greater flexibility in the choice of soil, with the result that a soil is selected which most closely matches the contamination of the equipment to be cleaned.

Certain soils, such as plasma and mucous, have little natural color, making visual or spectroscopic detection difficult. In one preferred embodiment, an additive or colorant, for example a dye or carbon black, is added to the soil to improve detection of remaining soil after cleaning. The additive may be detected by visual or spectroscopic means. Preferably the additive is one which is absorbed by the soil and is removed from the porous material, during the cleaning process, as the soil is removed.

Figure 2:
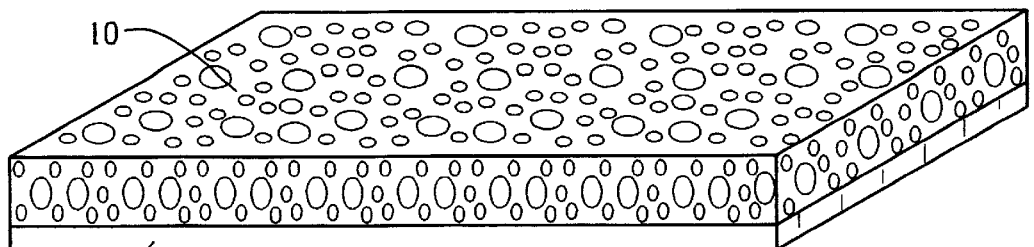
FIG. 2 illustrate a preferred embodiment of an apparatus or devices for the assessment and validation of cleaning processes in accordance with the present invention.

With reference to FIG. 2, suitable, porous materials include sintered or foamed metals, ceramics, open celled expanded plastics, plastic foams, and the like. A particularly preferred material is an expanded polyolefin matrix or foam. The material is preferably pigmented white or another color that provides strong contrast with the selected soil. The porous material is preferably selected to create a structure which is at least as challenging to the cleaning process as the medical equipment to be cleaned.

With reference to FIG. 2, in one alternative embodiment for an apparatus for the assessment and validation of cleaning, the porous material 10 is backed by an impermeable material or wall 30. The impermeable layer limits penetration through the one surface making removal of the soil by the cleaning process more difficult. The impermeable material 30 defines a plate having at least one surface. The porous material 10 is disposed on at least one surface of the plate.

Figure 3:
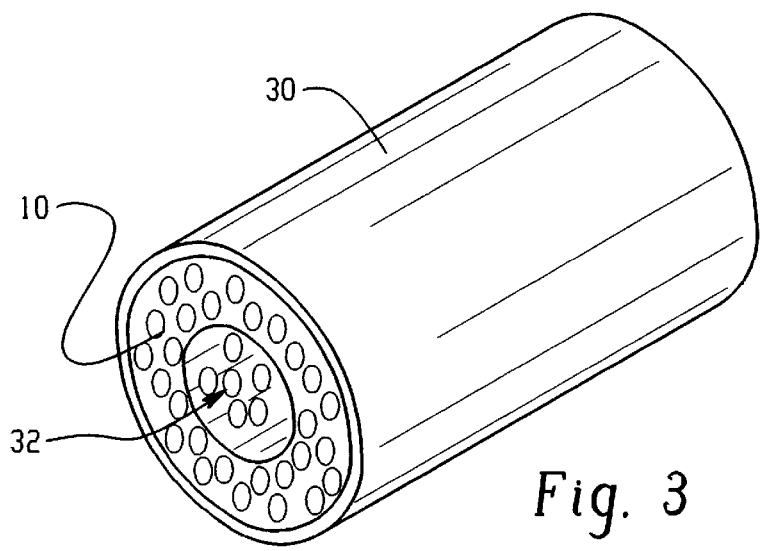
FIG. 3 illustrate an other embodiment of an apparatus or devices for the assessment and validation of cleaning processes in accordance with the present invention.

In FIG. 3, the porous material 10 defines a tube with at least one open end and a hollow interior 32. The impermeable layer 30 surrounds the tube. The tubular construction simulates a particularly difficult to clean piece of medical equipment such as an endoscope or other device containing lumen. In the illustrated embodiment, the porous material is disposed on the inner surface of the tube, although other methods of disposition are also contemplated. In one preferred embodiment, the tube has an open end which is connected to one end of a piece of medical equipment having a lumen such that the porous material is subject to substantially the same cleaning conditions as the interior of the lumen.

The porous material is preferably disposed on the plate or within the tube created by the impermeable wall, in such a way that it is not affected during the cleaning process.

The wall is preferably constructed of a material which is impenetrable to the chemicals used in the cleaning process, thereby creating a barrier which resembles the difficult to clean areas of medical equipment.

A number of methods for the analysis of residual soil are currently known in the art, for example visual inspection, spectroscopic means, chemical extraction and microbiological analysis.

Where the assessment of the cleaning process is to be made spectroscopically, the porous material and the impermeable wall are preferably constructed of materials which do not generate spectral bands in the same regions as the soil used.

Where the assessment of cleaning effectiveness is to be made visually, the porous material is preferably of a contrasting color to the soil so that the presence of soil may be detected more easily. For improved visual inspection, the impermeable wall, where present, is preferably in the shape of a plate or in the shape of a tube can be opened to permit inspection.

Where the method of assessment is microbiological, a calibrated population of a microorganism is added to the soil before cleaning. The presence of viable microorganisms after cleaning is an indication that the cleaning was inadequate. Preferably the microorganism selected is one which is not destroyed during the cleaning process.

Figure 4:
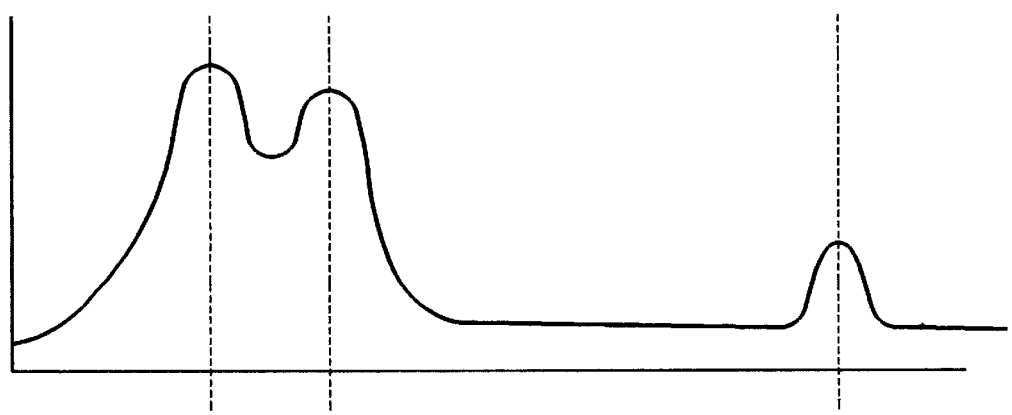
FIG. 4 illustrates an exemplary soil spectrum.

With reference to FIG. 4, a typical infrared spectra of the selected soil will have two or more reflection or absorption such as $\lambda_1, \lambda_2$. The wavelength and amplitude of the peaks, of course, vary with the selected soil. Preferably, the porous material 10 also has one or more peaks such as at wavelength $\lambda_3$. Typically, when the porous media is soiled, the soil prevents the infrared light from reaching the media and the peak $\lambda_3$ is suppressed. When the porous media is cleaned, the peaks $\lambda_1, \lambda_2$ from the soil are eliminated and the peak $\lambda_3$ from the porous material is strongly present.

Figure 5:
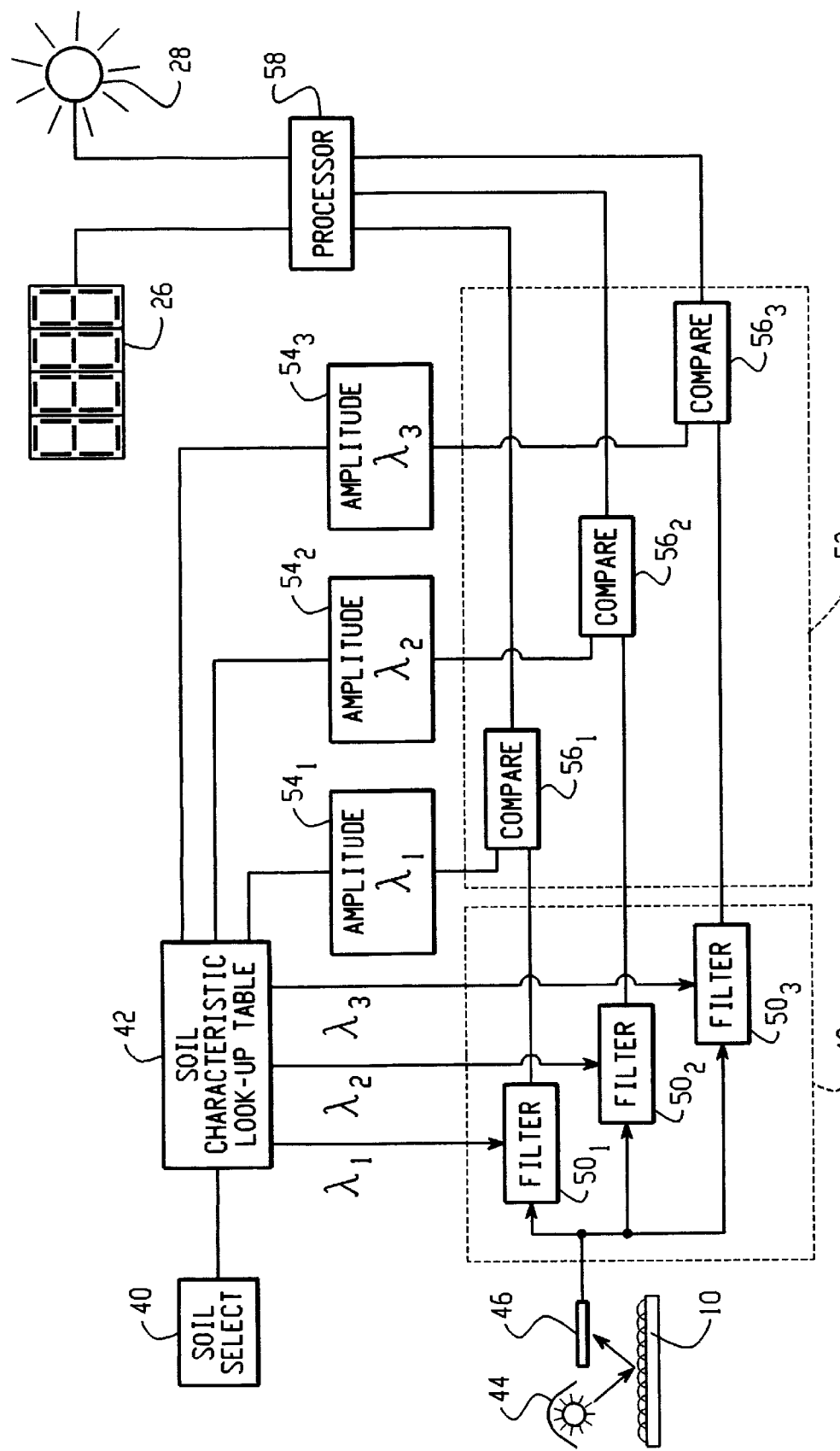
FIG. 5 illustrates an exemplary reader for evaluating the devices of FIGS. 1, 2, and 3.

With reference to FIG. 5, an operator uses an input device such as a keyboard or touch screen 40, to select one of a plurality of potential soil types. A soil characteristic look-up table 42 is preprogrammed with the characteristic peaks of the selected soil and of the porous media substrate. For simplicity of illustration, three peaks are illustrated in FIG. 5. Of course, a larger number of peaks can also be used for more assured accuracy.

An infrared light source 44 is focused to illuminate the porous material 10. Light reflected from the porous material is received by a photodetector 46. It is contemplated that the reader may work with either reflected photo peaks or with absorption peaks. The electronic signal from the photodetector is processed 48 to divide the signal into components indicative of the peaks of the selected soil and porous material.

More specifically to the illustrated embodiment, the characteristic wavelengths retrieved from the soil characteristic look-up table are communicated to a series of filters $50_1$, $50_2$, $50_3$, one for each of the retrieved characteristic wavelengths. The filters are received by the characteristic wavelengths to pass the portion of the received photosignal attributable to the corresponding peak. In this manner, a signal indicative of the amplitude of the received light which each of the characteristic wavelengths is produced.

The magnitude of the component of each characteristic wavelength is analyzed 52 to determine from the components strengths at each characteristic wavelength whether the porous material has been cleaned or the degree of soil reduction. In the illustrated embodiment, a series of memories $54_1$, $54_2$, $54_3$ are programmed by the soil characteristic look-up table 42 with projected magnitudes for each of the characteristics wavelength signals. Comparators $56_1$, $56_2$, $56_3$ compare the magnitude of the photosignal at each wavelength with the anticipated amplitude to determine a deviation therebetween. A processor 58 processes the relative amplitudes of each component, such as with a best fit routine which tries to fit the relative amplitudes with infrared spectrum curves of a completely clean porous material, a fully soiled porous material and possibly of curves of intermediate cleanliness or soil reduction. Based on the degree of fit or other analysis, the processor 58 produces an output display 26 indicative of the degree of cleanliness, e.g. a percentage of residual soil. Alternately, the processor 58 can make a simple soiled/non-soiled decision and illuminate an indicator light 28 indicating whether the porous material was satisfactorily cleaned.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method for assessment and evaluation of a cleaning process comprising the steps of:
   a) contaminating a porous material with a known soil, the porous material including a tortuous path for providing a challenge to cleaning wherein said challenge is selected to be comparable to that provided by medical equipment that is difficult to clean;
   b) subjecting the porous material and the soil to a cleaning process to be assessed and evaluated, the cleaning process being one which is intended to remove the soil from surfaces of said medical equipment to be cleaned; and,
   c) evaluating the cleaning process by evaluating the porous material for presence of remaining soil which has not been removed during the cleaning process.

2. The method of claim 1 further including:
   disposing the porous material and the soil in a sealed shipping package.

3. The method of claim 1, wherein the step of contaminating the porous material includes:
   introducing the soil to the porous material in the form of a slurry and drying the soil.

4. The method of claim 1, wherein the cleaning process includes a decontamination process selected from the group consisting of washing, disinfecting, sterilizing, and combinations thereof.

5. The method of claim 1, wherein the step of evaluating the porous material for the presence of remaining soil includes evaluating by a method selected from the group consisting of visual examination, spectroscopic analysis, chemical extraction, microbiological analysis, and combinations thereof.

6. A method for assessing and evaluating a cleaning process comprising;
   a) bonding a layer of a fluid-impermeable material to a porous material;
   b) forming the bonded porous material and impermeable layer in a tubular shape with at least one internal passage lined by the porous material;
   c) contaminating the porous material with a known soil;
   d) subjecting the porous material, the impermeable layer, and the soil to a cleaning process to be assessed and evaluated, the cleaning process being one which is intended to remove the soil from items to be cleaned;
   e) evaluating the cleaning process by evaluating the porous material for remaining soil which has not been removed during the cleaning process.

7. A method for assessment and evaluation of a cleaning process comprising:
   a) contaminating porous material with a known soil, the porous material generating at least one porous material spectral band and the soil generating at least one soil spectral band when illuminated by light in the infrared range;
   b) subjecting the porous material and the soil to a cleaning process to be assessed and evaluated, the cleaning process being one that is intended to remove the soil from items to be cleaned;
   c) evaluating the cleaning process by evaluating the porous material for remaining soil by spectroscopic analysis including:
      illuminating the porous material with light in the infrared range;
      receiving infrared light reflected from the porous material and generating an electrical signal indicative of the porous material and the remaining soil;
      separating components of the electrical signal attributable to said at least one porous material spectral band and said at least one soil spectral band;
      analyzing the components of said electrical signal attributable to each of said spectral bands to generate an output display representative of residual soil remaining on said porous material after said cleaning process.

8. A method for assessment and evaluation of a cleaning process for cleaning of medical equipment comprising:
   a) contaminating a porous material with a known soil, the porous material having an internal passage comprising a tortuous path which simulates medical equipment to be cleaned;
   b) subjecting the medical equipment, the porous material, and the soil to a cleaning process to be assessed and evaluated, the cleaning process being one which is intended to remove the soil from surfaces of said medical equipment items to be cleaned; and,
   c) evaluating the efficacy of the cleaning process for cleaning the medical equipment by evaluating the porous material for presence of remaining soil which has not been removed during the cleaning process.

9. The method of claim 8, wherein the said internal passage includes an expanded polyolefin matrix or foam for collecting said known soil.

10. The method of claim 8, wherein the porous material is formed in a tubular shape and wherein during the cleaning process, the porous material is interconnected with a lumen of said medical equipment being cleaned such that the lumen and the internal passage of said porous material are fluidly interconnected.

11. A method for assessing and evaluating a fluid cleaning process comprising the steps of:
   a) rendering at least one surface of a porous material impermeable to penetration of fluids employed in the cleaning process;
   b) contaminating the porous material with a known soil;
   c) subjecting the porous material and the soil to a fluid cleaning process to be assessed and evaluated, the process being one which is intended to remove the soil from items to be cleaned;
   d) evaluating the cleaning process by evaluating the porous material for remaining soil which has not been removed by the fluid.

12. The method of claim 11, wherein the step of rendering said at least one surface impermeable to the penetration of fluids includes bonding a layer of impermeable material to the porous material.

13. A method for assessment and evaluation of a cleaning process comprising the steps of:
   a) incorporating an additive into a known soil and contaminating a porous material with the soil;
   b) subjecting the porous material, the soil, and the additive to a cleaning process intended to remove the soil from surfaces of items to be cleaned;
   c) evaluating the cleaning process by
      (i) examining the porous material for presence of remaining soil and detecting residual additive which has not been removed during the cleaning process.

14. The method of claim 13, wherein the additive is a colorant selected from the group consisting of dyes, carbon black, and combinations thereof.

* * * * *